US012427246B2

(12) United States Patent
Holmqvist

(10) Patent No.: US 12,427,246 B2
(45) Date of Patent: Sep. 30, 2025

(54) MEDICAMENT DELIVERY DEVICE

(71) Applicant: SHL MEDICAL AG, Zug (CH)

(72) Inventor: Anders Holmqvist, Värmdö (SE)

(73) Assignee: SHL Medical AG, Zug (CH)

( * ) Notice: Subject to any disclaimer, the term of this patent is extended or adjusted under 35 U.S.C. 154(b) by 948 days.

(21) Appl. No.: 17/418,379

(22) PCT Filed: Dec. 12, 2019

(86) PCT No.: PCT/EP2019/084854
§ 371 (c)(1),
(2) Date: Jun. 25, 2021

(87) PCT Pub. No.: WO2020/143987
PCT Pub. Date: Jul. 16, 2020

(65) Prior Publication Data
US 2022/0062533 A1 Mar. 3, 2022

(30) Foreign Application Priority Data
Jan. 7, 2019 (EP) .................................... 19150599

(51) Int. Cl.
*A61M 5/145* (2006.01)
*A61M 5/142* (2006.01)
*A61M 5/158* (2006.01)

(52) U.S. Cl.
CPC .......... *A61M 5/1454* (2013.01); *A61M 5/158* (2013.01); *A61M 5/14248* (2013.01);
(Continued)

(58) Field of Classification Search
CPC ................ A61M 5/1454; A61M 5/158; A61M 5/14248; A61M 2005/14252;
(Continued)

(56) References Cited

U.S. PATENT DOCUMENTS 5,261,882 A * 11/1993 Sealfon ............... A61M 5/1454
604/246
5,858,001 A 1/1999 Tsals et al.
(Continued)

FOREIGN PATENT DOCUMENTS

EP 2736565 A2 6/2014

OTHER PUBLICATIONS

International Search Report and Written Opinion for Int. App. No. PCT/EP2019/084854, mailed Mar. 24, 2020.

*Primary Examiner* — Rebecca E Eisenberg
*Assistant Examiner* — Neeraja Gollamudi
(74) *Attorney, Agent, or Firm* — McDonnell Boehnen Hulbert & Berghoff LLP

(57) ABSTRACT

The present application relates to a medicament delivery device comprising a housing, a medicament container holder arranged to accommodate a medicament container, a needle assembly comprising an injection needle part and a penetration needle part, wherein the extension of the injection needle part and the extension of the penetration needle part are angled generally 90 degrees, a penetration mechanism arranged to move the needle assembly in a direction generally coinciding with the extension of the injection needle part between an initial position of the injection needle part inside said housing to a penetration position with the injection needle part extending outside said housing; a medicament container connection mechanism arranged to move the medicament container holder and the medicament container in a direction generally coinciding with the penetration needle part for creating a flow passage from the interior of the medicament container to an outlet of the injection needle part.

20 Claims, 18 Drawing Sheets

(52) U.S. Cl.
CPC ............ *A61M 2005/14252* (2013.01); *A61M 2005/14256* (2013.01); *A61M 2005/1581* (2013.01)

(58) Field of Classification Search
CPC .. A61M 2005/1581; A61M 2005/1585; A61M 2005/31518
See application file for complete search history.

(56) References Cited

U.S. PATENT DOCUMENTS

| | | | |
|---|---|---|---|
| 6,364,865 B1* | 4/2002 | Lavi | A61M 5/2448 604/411 |
| 2009/0043278 A1* | 2/2009 | Tanaka | A61M 5/1452 604/138 |
| 2012/0123387 A1* | 5/2012 | Gonzalez | A61M 37/0015 604/506 |
| 2015/0080857 A1* | 3/2015 | Stroup | A61M 39/02 604/110 |
| 2016/0082182 A1* | 3/2016 | Gregory | A61M 5/14248 604/152 |
| 2016/0354553 A1* | 12/2016 | Anderson | A61M 5/19 |
| 2018/0236173 A1 | 8/2018 | McCaffrey et al. | |

* cited by examiner

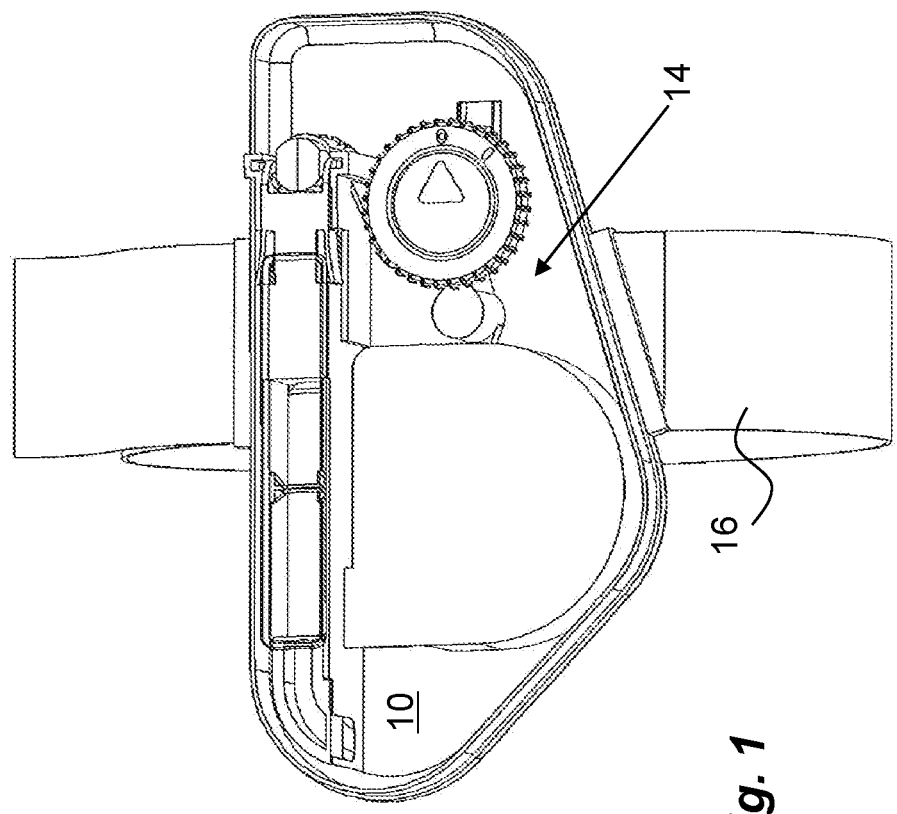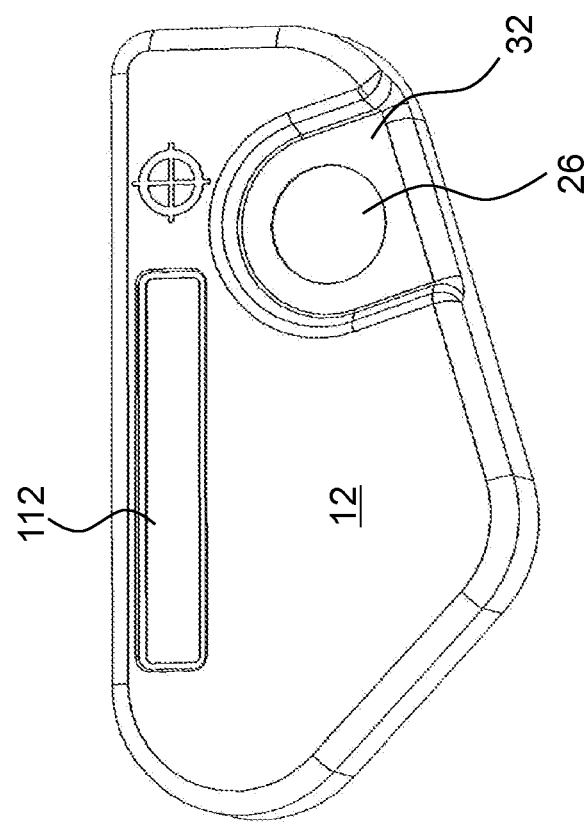
Fig. 1

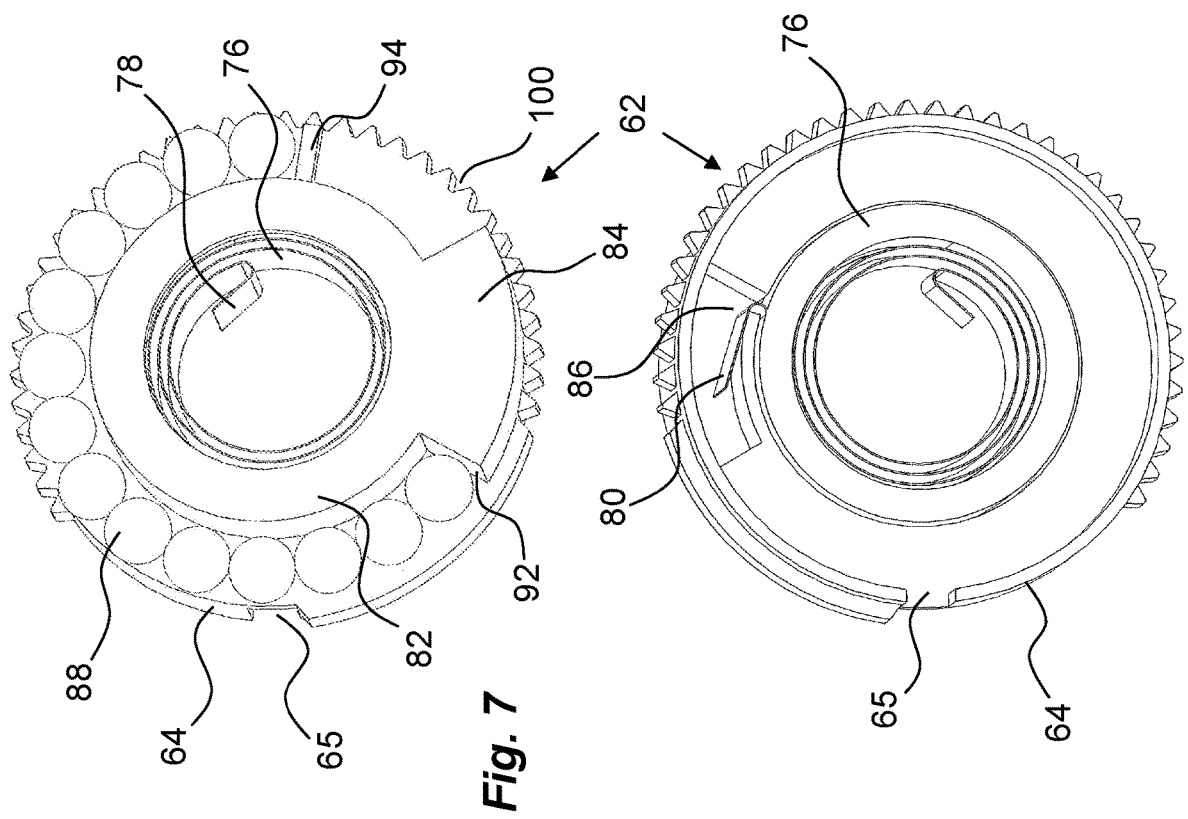
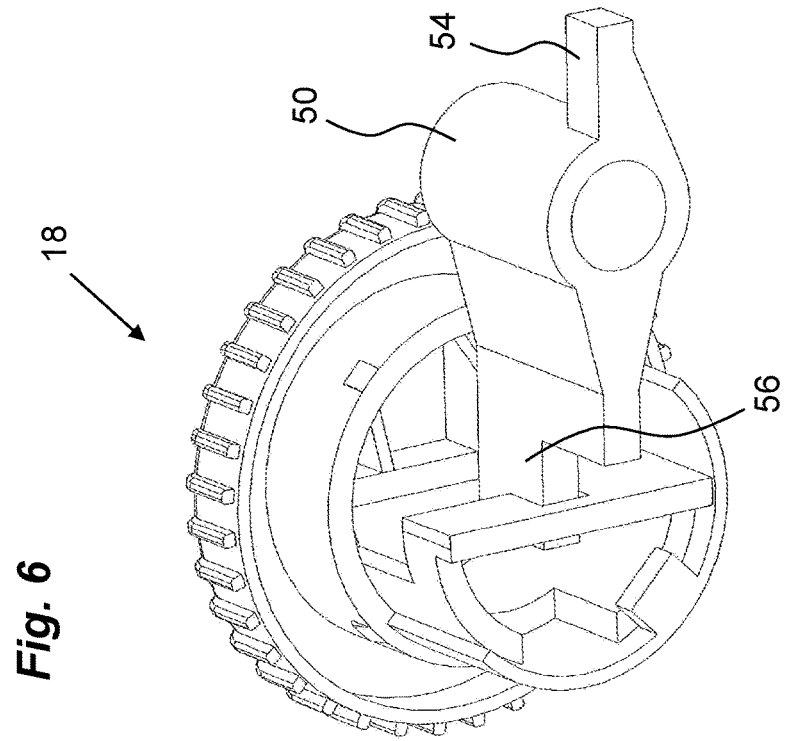

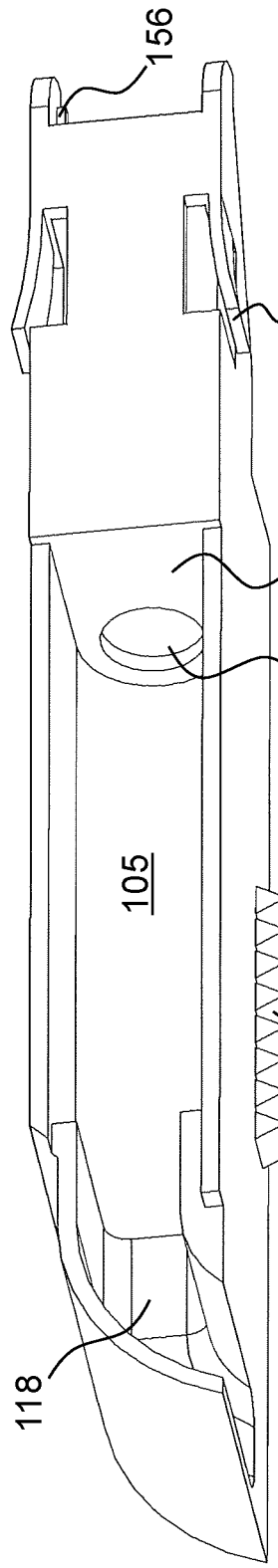
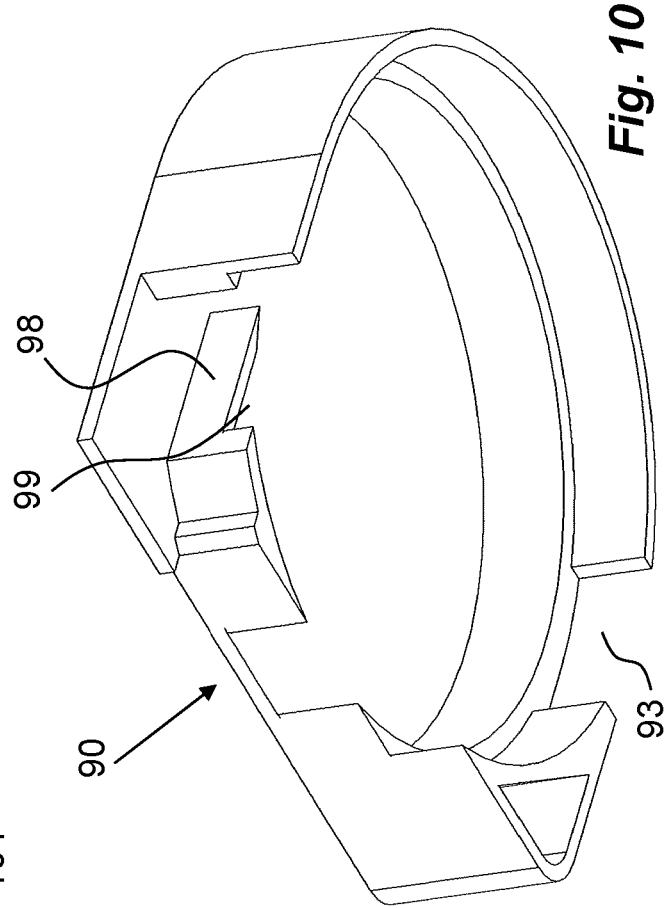
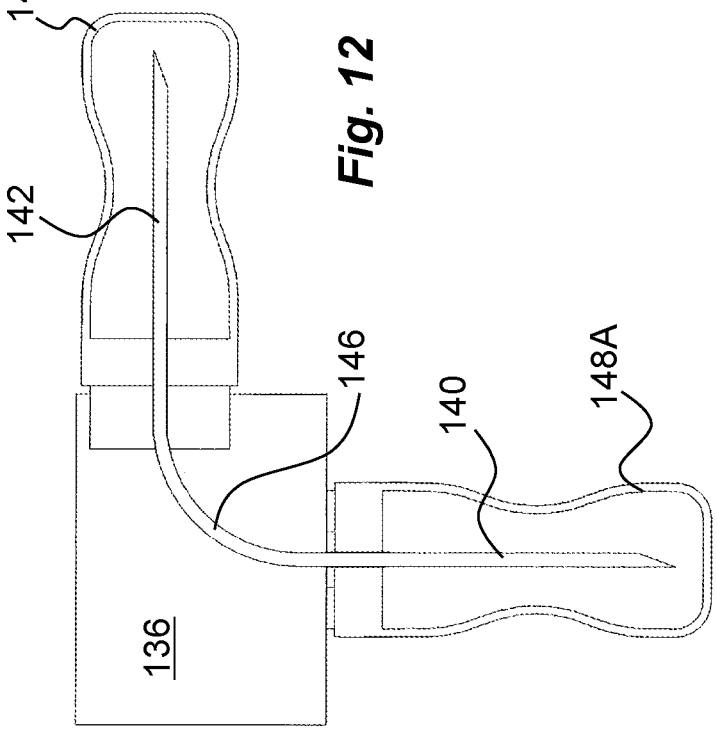

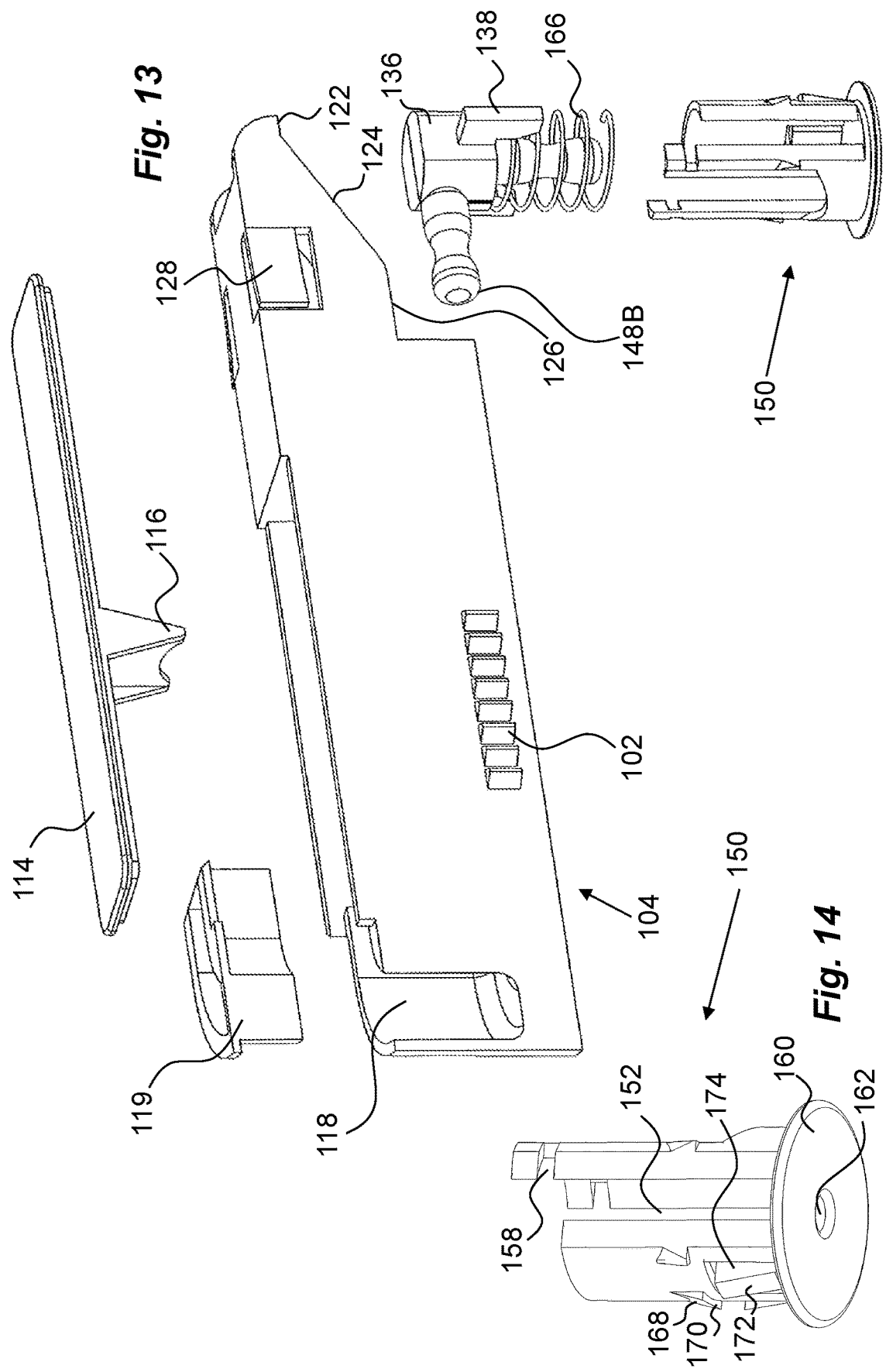

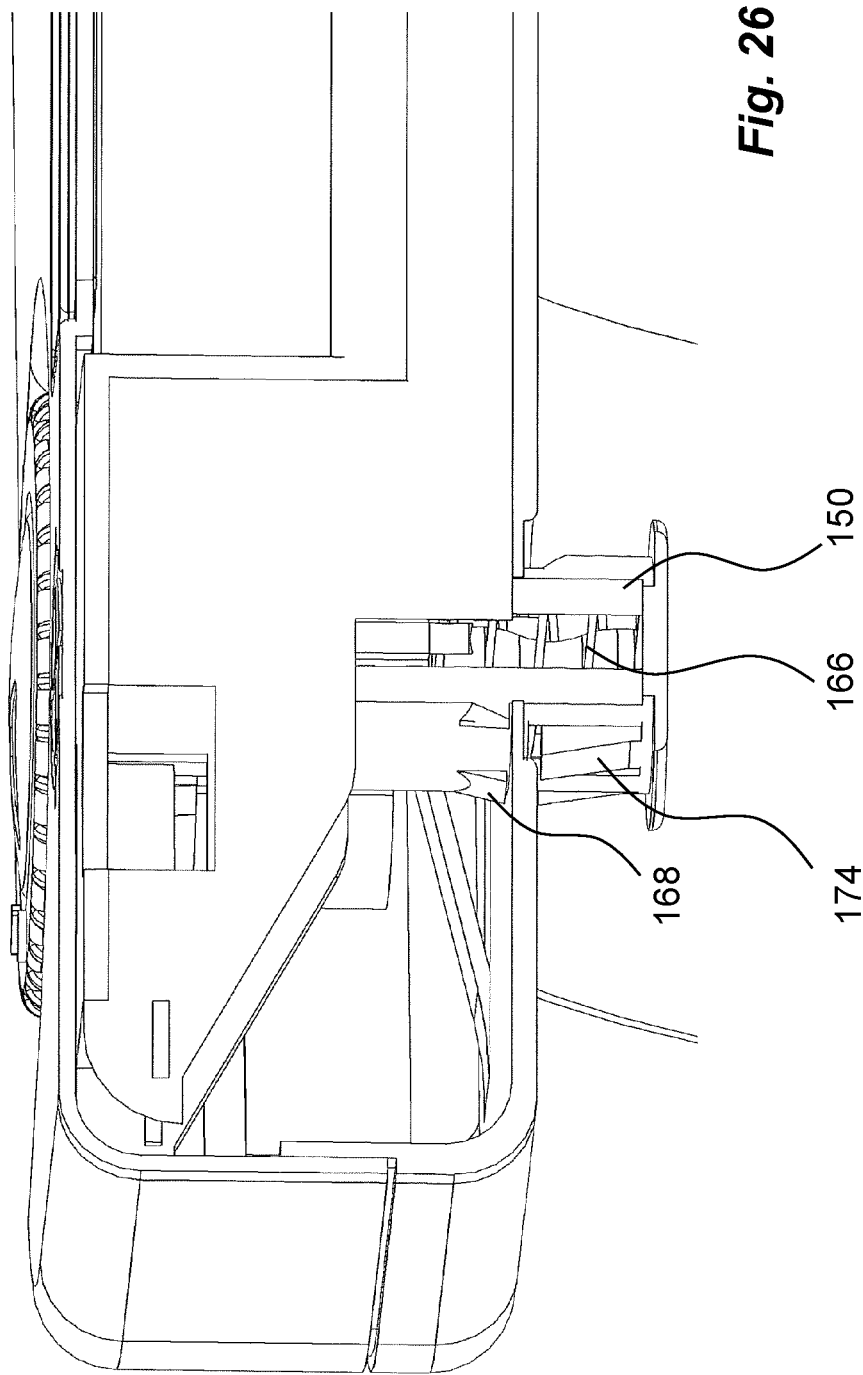

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2019/084854 filed Dec. 12, 2019, which claims priority to European Patent Application No. 19150599.9 filed Jan. 7, 2019. The entire disclosure contents of these applications are herewith incorporated by reference into the present application.

TECHNICAL AREA

The present disclosure relates to a medicament delivery device and in particular a medicament delivery device that can be worn on or attached to the body of a user during a dose delivery operation.

BACKGROUND

So called mini infusers are becoming more and more interesting with patients and users that are self-medicating as an alternative to more conventional pen injectors or auto-injectors. The mini infusers are generally rather compact and are designed to be attached to a body part of a user. When attached to a dose delivery area of the user, activation of the mini infuser will often perform an automatic penetration into the tissue by an injection needle and a subsequent automatic injection sequence. After performed dose delivery the mini infuser may then be removed.

One advantage with a mini infuser is that it often is compact and can be worn under clothes, and are then not visible to strangers when a user is in a public environment, which for some users is important. The mini infuser can then be activated without any other persons noticing it. This is a major difference to conventional elongated injectors that can hardly be hidden when used. The mini infuser may also be worn on the body for a long time until activation.

One challenge with the design of mini infusers is to have a high degree of automatic functionality while keeping the overall dimensions as small as possible and in particular the height or extension from the body. Users will generally not appreciate if the device protrudes too much or gives a bulky appearance so that the device could be noticeable even when worn under clothes. There is also a challenge to have such a high degree of functionality and at the same time keeping the number of components as low as possible.

Document EP 2 736 565 discloses a medicament delivery device that can be attached to the body of a patient or user. The medicament delivery device is arranged with an injection needle that can be extended from a housing to perform a penetration and can be retracted into the housing after performed injection. In order to perform the penetration, the needle is moved in a direction generally parallel to the injection site surface. The medicament delivery device is further arranged with a guide channel that has an inclination in relation to the injection site surface, wherein the front part of the needle is inserted into the guide and also has an inclination. When a penetration is to be performed the needle is moved along the inclined guide where the front end of the needle penetrates the skin of the patient. The movement will also cause the rear end of the needle to bend as it is introduced into the guide.

Bending of the needle is usually not positive since it is difficult to control the penetration direction. Further there is a risk that the needle is damaged due to the bending action. Therefore, this solution does not seem to be optimal. Further, the needle has a specially formed rear end that is bent 180 degrees. This is because the penetration movement of the needle also can cause a penetration of a septum of a medicament container placed on the side of the needle. In all, the needle solution of EP 2 736 565 does not seem to be optimal.

SUMMARY

In the present disclosure, when the term "distal" is used, this refers to the direction pointing away from the dose delivery site. When the term "distal part/end" is used, this refers to the part/end of the delivery device, or the parts/ends of the members thereof, which under use of the medicament delivery device is/are located furthest away from the dose delivery site. Correspondingly, when the term "proximal" is used, this refers to the direction pointing to the dose delivery site. When the term "proximal part/end" is used, this refers to the part/end of the delivery device, or the parts/ends of the members thereof, which under use of the medicament delivery device is/are located closest to the dose delivery site.

According to a main aspect of the disclosure a medicament delivery device is provided, comprising a housing and a medicament container holder arranged to accommodate a medicament container inside the housing. A needle assembly may further be arranged, comprising an injection needle part and a penetration needle part, wherein the extension of the injection needle part and the extension of the penetration needle part are angled generally 90 degrees.

A penetration mechanism may further be arranged to move the needle assembly in a direction generally coinciding with the extension of the injection needle part between an initial position of the injection needle part inside said housing to a penetration position with the injection needle part extending outside said housing. Moreover, a medicament container connection mechanism may be arranged to move the medicament container holder and the medicament container in a direction generally coinciding with the penetration needle part for creating a flow passage from the interior of the medicament container to an outlet of the injection needle part.

Thus the needle assembly is arranged with two needle part that are angled in relation to each other which provides the advantage that the medicament container can be positioned generally parallel with the dose delivery surface while the injection needle part is perpendicular to the dose delivery surface. This solution will provide a low height of the medicament delivery device.

The medicament delivery device may further comprise a drive mechanism comprising a rotator, arranged to be rotated by a tensioned drive spring and drive elements arranged between the rotator and the needle assembly for causing a penetration of the injection needle part. The use of a rotator will also provide the advantage that is may provide a number of functions with few components.

According to one aspect of the disclosure, the drive elements may comprise the medicament container holder operatively connected between the rotator and the needle assembly. Thus, the medicament container holder is used as such for driving the needle assembly. In that respect, the medicament container holder may comprise a transfer element acting on the needle assembly such that movement of the medicament container holder by the rotator causes a penetrating movement of the needle assembly.

Further, the transfer element may comprise surfaces that are inclined in relation to the movement direction of the medicament container holder and the movement direction of the needle assembly, which inclined surfaces are acting on support surfaces of the needle assembly.

Moreover, the drive mechanism may comprise teeth on the rotator acting on a toothed rack on the medicament container holder. Further, the drive mechanism may comprise a number of discrete elements placed around the circumference of the rotator and operatively connected to the rotator, wherein rotation of the rotator causes the discrete elements to move and to act on a stopper of the medicament container for expelling a dose of medicament. Thus, as seen from the above, the rotator is capable of providing a number of functions with few components and elements. The discrete elements may comprise spherical bodies.

The drive mechanism may further comprise guide elements for guiding the discrete elements between the rotator and the medicament container holder for acting on the stopper. Regarding the function of the medicament delivery device, the rotator may be designed such that that interaction with the medicament container holder for performing a penetration is completed when the discrete elements begin acting on the stopper. This ensures that the penetration is completed before any injection is activated.

According to another aspect of the V, it may further comprise an activation unit operatively connected to the rotator for releasably holding the drive spring in a tensioned state. In this regard, the activation unit may comprise a manually operable activator, which upon manual activation, releases the rotator. As a further safety aspect, the activation unit may further comprise a lock element for releasably locking the activator.

According to a further aspect, the activation unit may further comprise an activating element in the form of a pivoting arm, wherein one end of the arm is releasably engaging the rotator and the other end of the arm is releasably engaging the activator. Further, the pivoting arm, after release of the rotator, may be in contact with a profiled surface of the rotator for creating an indication of the operation of the medicament delivery device.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which FIG. 1 is a side view of a medicament delivery device according to the present application with a housing part disassembled.

DETAILED DESCRIPTION

Figure 2:
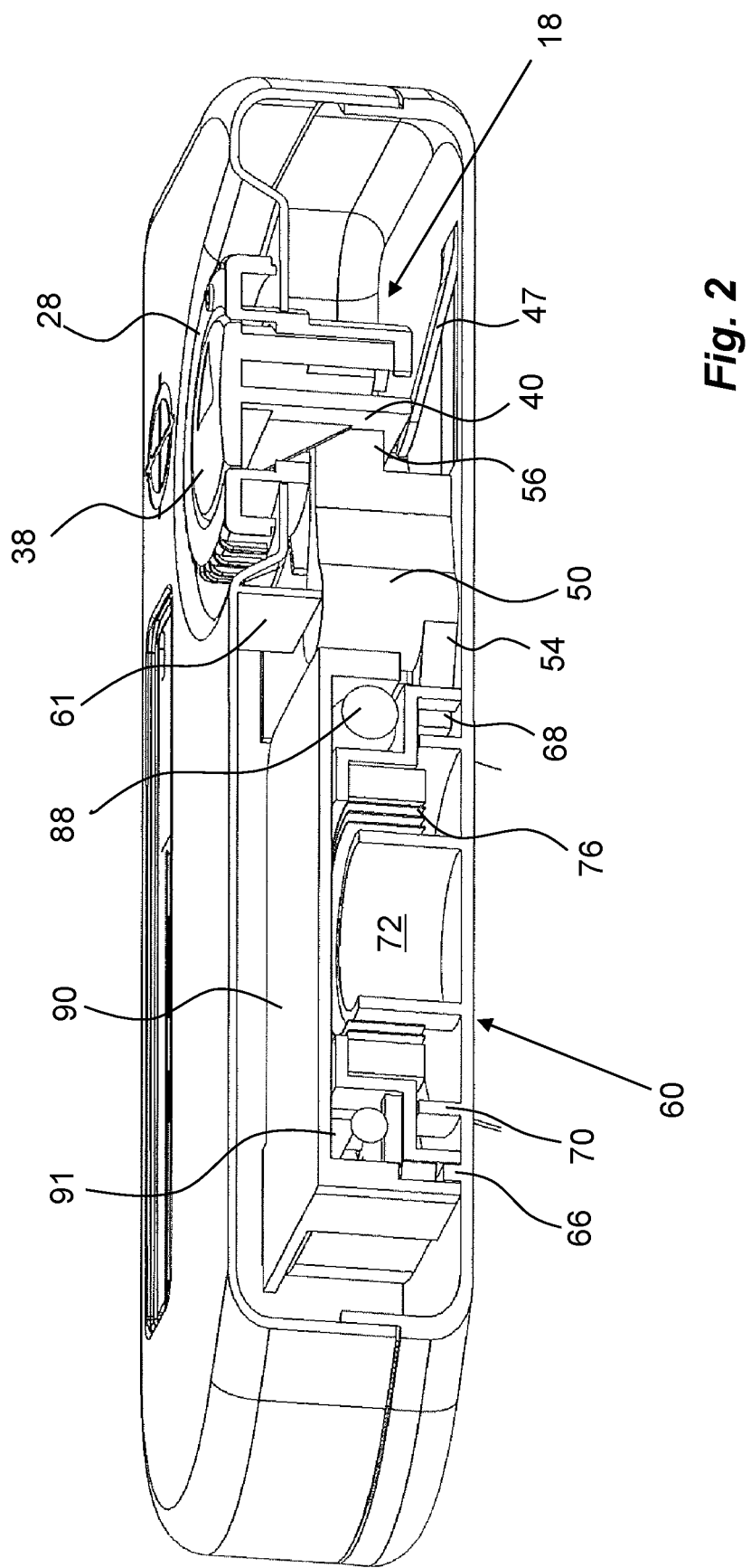
FIG. 2 is a cross-sectional view of the medicament delivery device of FIG. 1, FIGS. 3, 4, 5, 6, 7, 8, 9, 10, 11, 12, 13 and 14 are views of different components comprised in the medicament delivery device of FIG. 1.
Figure 5:
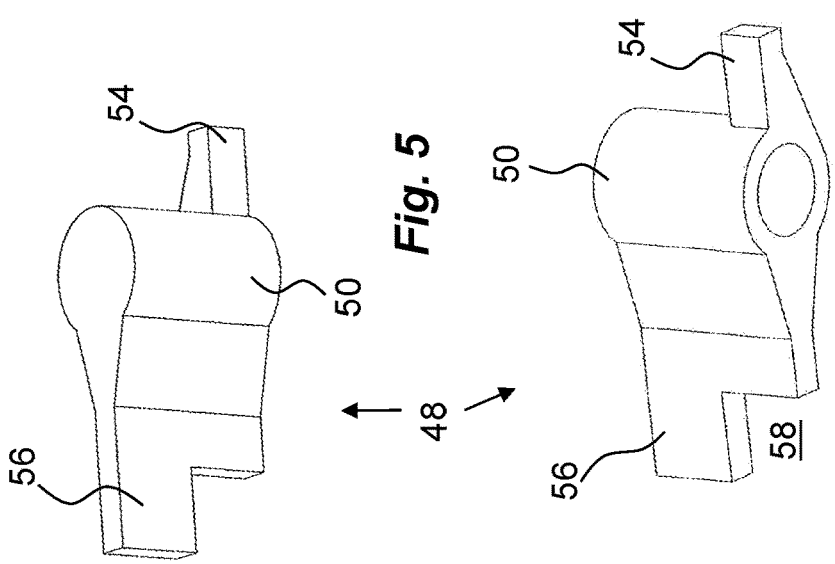
Figure 4:
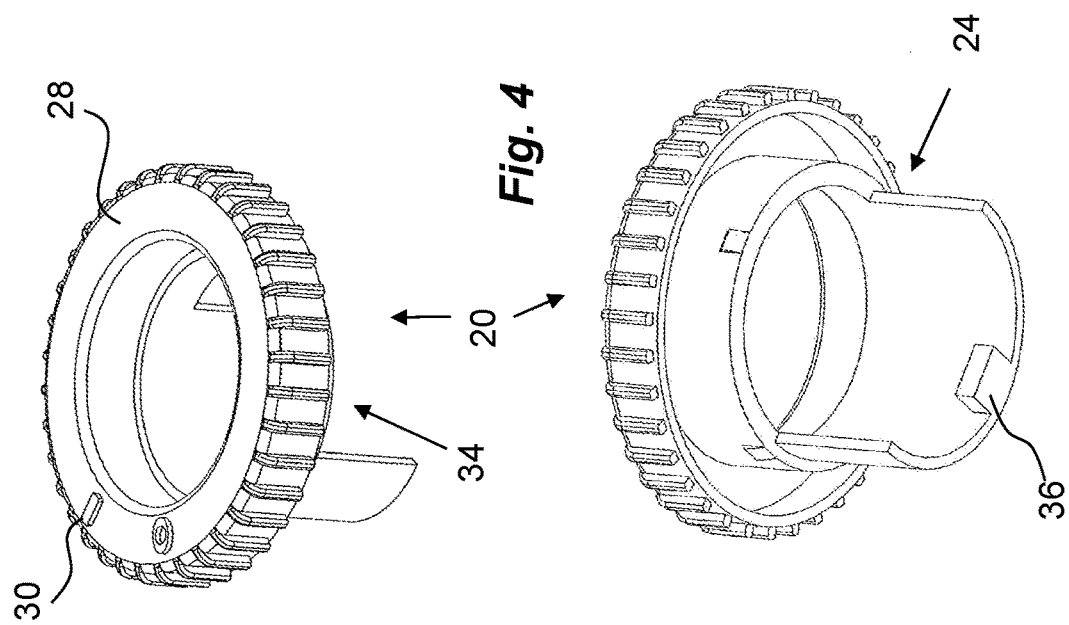
Figure 3:
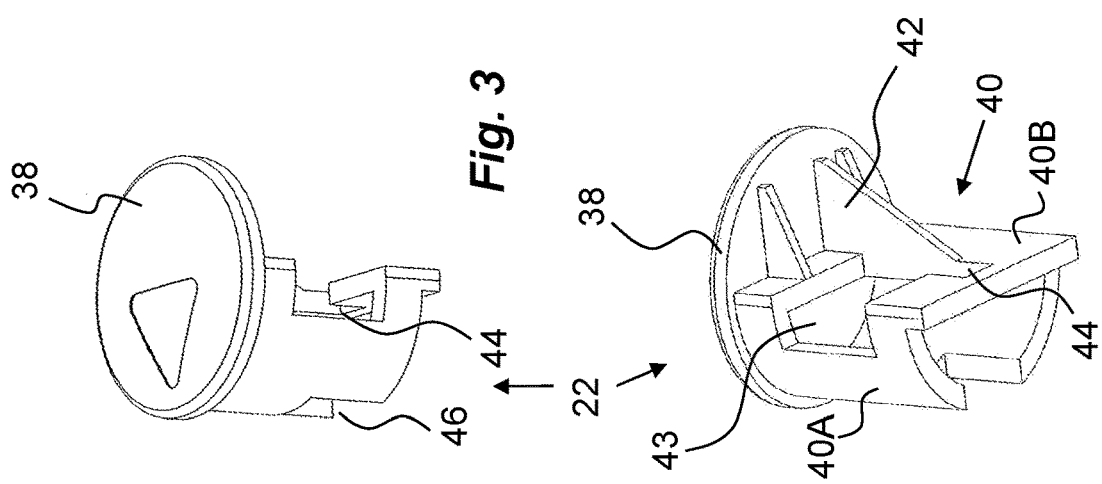

In the following description, the word proximal and proximal direction is intended to define directions towards a user or patient when the medicament delivery device is in use, and distal and distal direction is intended to define directions away from a user.

The medicament delivery device shown in the drawings comprises a lower base or first proximal housing part 10 and an upper cover or second distal housing part 12. The proximal housing part 10 is intended to be in contact with a body part of a patient or user, where the second distal housing part 12 is attached to the first proximal housing part 10, both forming an interior where a medicament delivery mechanism 14 is arranged. The proximal housing part 10 is provided with a suitable attachment arrangement that in the embodiment shown comprises a band 16, preferably elastic and/or adjustable to fit around a body part such as an arm or leg, or maybe even the waist. Instead of a band, the outer surface of the first housing part may be arranged with an adhesive layer so that the medicament delivery device can be attached to a suitable part of the body of the patient.

The medicament delivery mechanism 14 comprises an activation unit 18, FIGS. 2-5, which activation unit 18 comprises a lock element 20 and an activator 22. The lock element 20 comprises a generally tubular body 24 that extends through a passage 26 in the distal housing part 12. The body 24 is arranged with an annular grip ring 28, FIG. 4, that may be arranged with grip enhancing protrusions. The outwardly facing surface of the grip ring 28 is arranged with indicia 30 such as "0" and "1", the function of which will be explained. The grip ring 28 is accessible from the outside of the medicament delivery device where an inwardly directed surface of the grip ring 28 is in contact with a surface 32 of a slight recess, FIG. 1, in the distal housing part 12. The proximal part of the body 24 is arranged with a semi-circular cut-away 34. The remaining part of proximal end of the body is provided with a radially inwardly directed protrusion 36.

Inside the tubular body of the lock element 20 the activator 22 is placed. It comprises a generally disk-shaped contact element 38 that will act as contact surface for a user to activate the medicament delivery device as will be described. The activator 22 is further arranged with a body 40 extending in the proximal direction. The body 40 has a semi-circular part 40A and flat part 40B. Reinforcing ribs 42 are arranged between the contact element 38 and the flat part 40B. The body 40 is arranged with a first generally rectangular cut-out 43 extending from the semi-circular part 40A to the flat part 40B adjacent a reinforcing rib 42. A rectangular second cut-out 44 is extending in the proximal direction from the first cut-out 43. A third cut-out 46 is extending in the distal direction from the proximal end of the semi-circular part 40A. The activator 22 is urged in the distal direction by a resilient member 47, FIG. 2, that in the embodiment shown may be a section of the first housing part 10 being inclined distally and abutting a proximal end of the activator, causing a spring action. It is however to be understood that other types of resilient members such as compression springs may be utilized.

Figure 8:
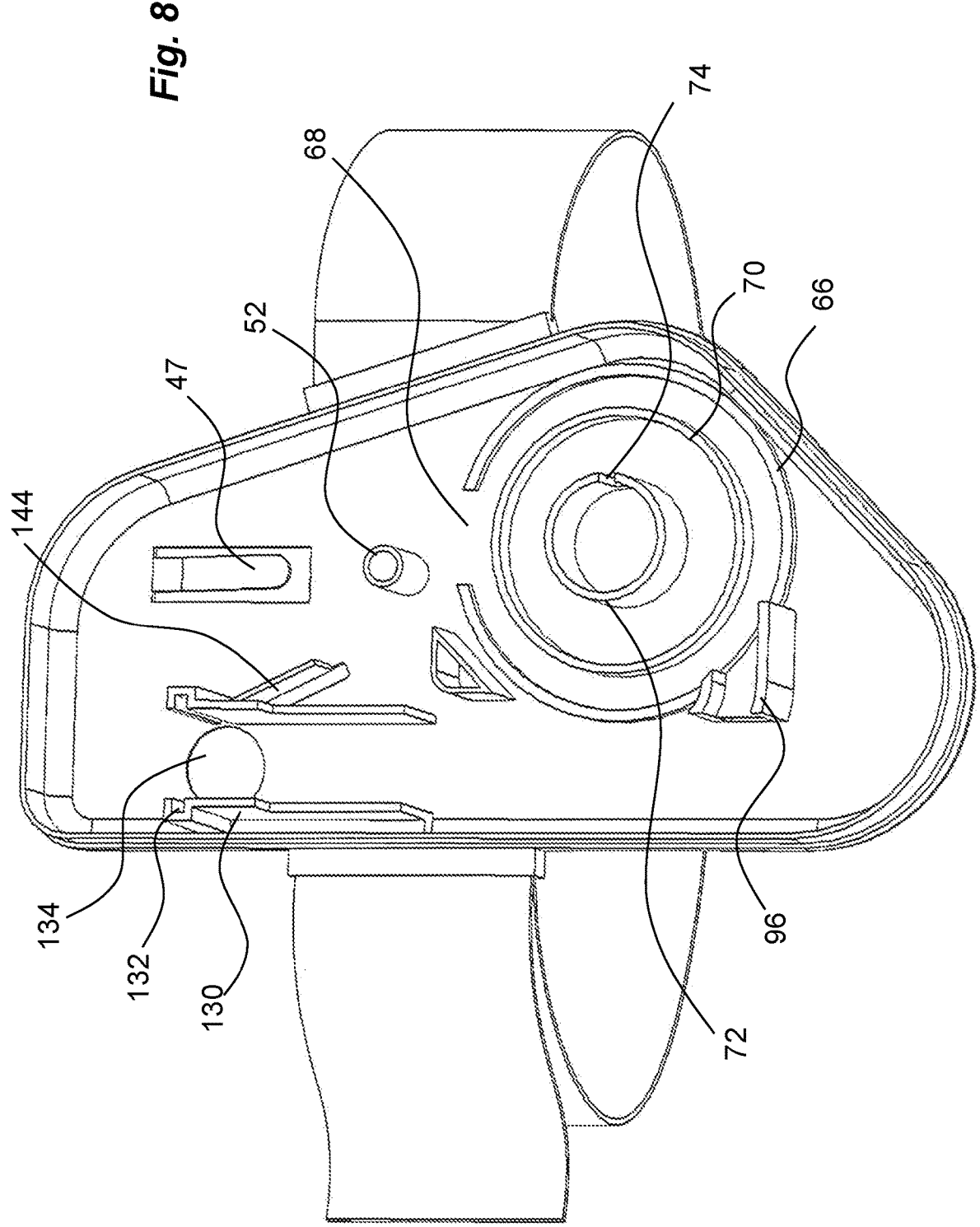

Further an activating element 48 is provided with a generally tubular hub 50 that is intended to fit onto and rotate around a post 52, FIG. 8, being a part of the inner surface of the proximal housing part 10. The hub 50 is arranged with a first arm 54 extending radially from a lower part thereof. Furthermore, the hub 50 is arranged with a second arm 56. The second arm 56 is arranged with a rectangular cut-out 58. The radial extending part of the second arm 56 is in the initial state intended to fit into the second cut-out 44 of the activator 22, FIGS. 2 and 6. The hub 50 is held in position on the post 52, i.e. prevented from moving in the distal direction by a proximally directed support wall 61, FIG. 2, on the second housing part. The first arm 54 is intended to interact with a drive unit 60.

The drive unit 60 comprises a disc-shaped rotator 62, FIG. 7, provided with a circumferential side surface 64. The side surface 64 is arranged with an opening 65 in which the first arm 54 extends in an initial position, causing a rotational lock of the rotator 62. The lower edge of the side surface 64 is arranged to be in contact with the inner surface of the proximal housing part 10. Further the proximal housing part 10 is arranged with a circular first ledge 66, FIG. 8, that the side surface 64 is in contact with, providing a guide for the rotator 62 as it rotates as will be described. The first ledge 66 is arranged with a cut-out 68 through which the first arm 54 extends in the initial position. Inside the first ledge 66 and concentrically arranged is a second ledge 70 acting as a support in the proximal direction for the rotator 62. Inside the second ledge 70 and coaxial therewith is a third ledge 72, FIGS. 2 and 6. The third ledge 72 is arranged with a slit 74. A clock spring 76, FIG. 7, is wound around the third ledge 72 having an inner end 78 provided with a 180-degree bend and fitting into the slit 74 whereby the inner end of the clock spring 76 is locked to the third ledge 72. The outer end 80 of the clock spring 76 is also arranged with a 180-degree bend. Further the rotator 62 is arranged with a hub 82 in which the clock spring 76 is placed. The hub 82 is connected to a compartment 84 provided with an opening 86 through which the bend of the outer end 80 of the clock spring 76 fits. Thus when the clock spring 76 is tensioned, it is capable of turning the rotator 62 as will be described.

On the opposite side of the rotator 62 a number of discrete elements in the form of spherical balls 88 are placed around the hub 82. The balls 88 are held in position around the hub 82 by a lid 90 that fits around the first ledge of the first housing part, preferably being in contact with an outwardly surface of the first ledge 66 creating a press fit to hold the lid 90 in place. The lid 90 and the hub 82 thus form a semi-circular channel 91, FIG. 2, that starts with a side wall 92, FIG. 7, of the compartment 84. The lid 90 is further arranged with an opening 93, FIG. 10, that fits together with the cut-out 68 of the first ledge 66. It should be noted that, alternatively, the spherical balls 88 can be replaced by a flexible wire with plunger head or segments connected plunger.

Figure 9:
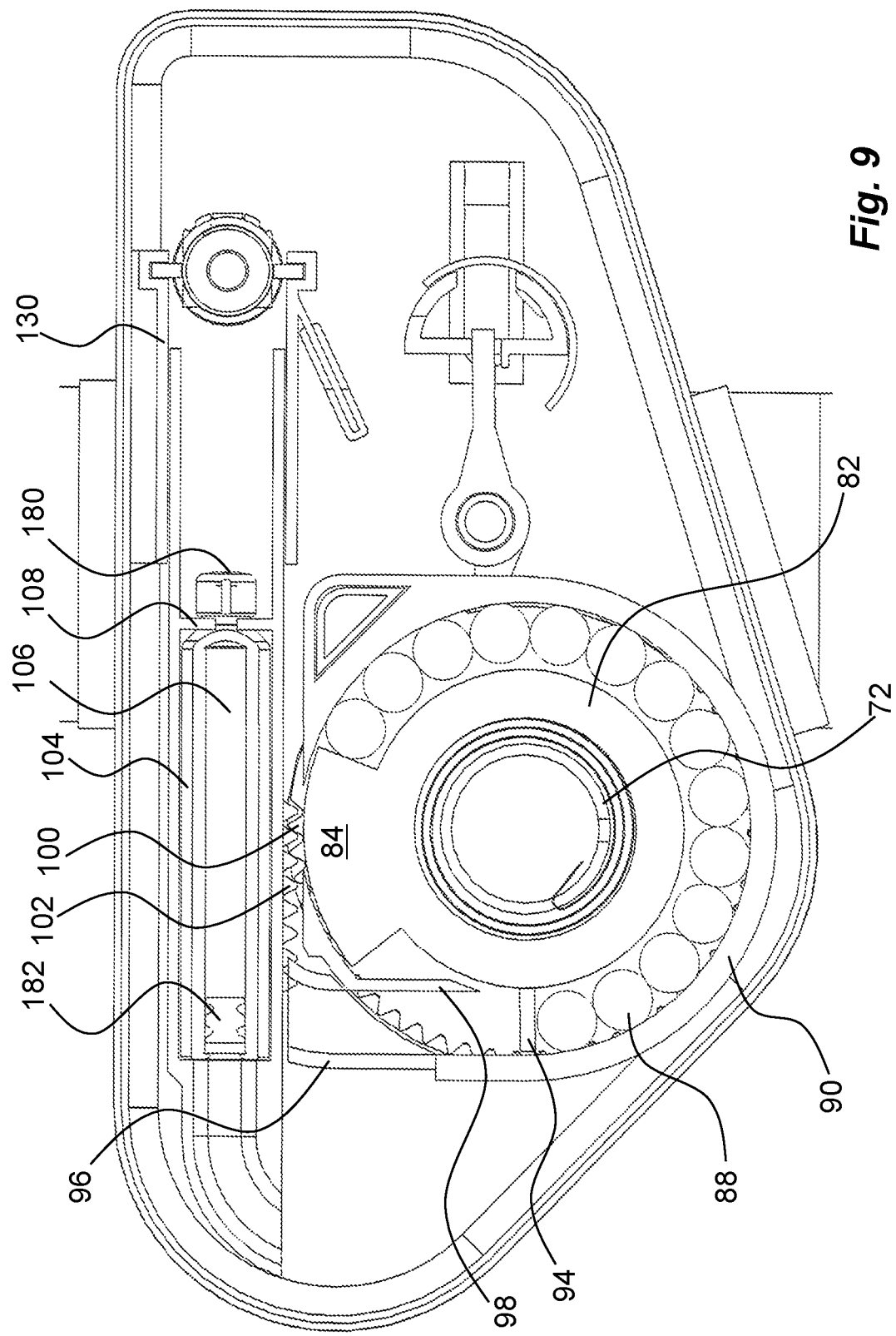

A radially extending stop ledge 94 is arranged from the hub 82 such that the balls 88 are positioned from the side wall 92 and to the stop ledge 94, FIG. 7. The stop ledge 94 is high enough to hold the balls 88 in this position. Guide walls 96, FIG. 9, are further provided on the first housing part 10 directed adjacent the rotator 62 and in a generally tangential direction. Also the lid 90 is arranged with a guide wall 98 as seen in FIGS. 9 and 10. The guide wall 98 is provided with a cut-out 99 through which the stope ledge 94 can pass when the rotator 62 is rotating.

The side surface 64 of the rotator 62 is further arranged with gear teeth 100 around a part of its circumference. These gear teeth 100 are arranged to interact with a gear rack 102 on an outer surface of an elongated medicament container holder 104. The medicament container holder 104 has a compartment 105, FIG. 11, designed to accommodate a medicament container 106. In this regard, the medicament container holder 104 is arranged with a transversal wall 108 having a passage 110 such that a neck portion of the medicament container 106 is held by the wall 108. The distal housing part 12 is arranged with an elongated opening 112 providing access to the medicament container holder 104 for placing a medicament container 106 in the medicament container holder 104. A protective lid 114, FIG. 13, is arranged to be placed in the opening, which protective lid 114 may be arranged with a proximally directed support element 116 designed to be in contact with and support the medicament container 106. The protective lid may be made of a transparent material so that a medicament container 106 placed in the medicament container 104 holder can be viewed.

Further, the rear end of the medicament container holder 104, FIGS. 11 and 13, is arranged with a channel 118 that is curved almost 90 degrees and having an opening at its rear end. A lid 119 is arranged to be placed in the channel 118 for limiting the channel area. A front end of the medicament container holder 104 is provided with side walls that form extensions 120 directed in a forward direction, FIG. 13, which extensions 120 will function as transfer elements as will be described. The extensions 120 are provided with a first proximally directed edge 122 arranged generally parallel with the extension of the medicament container holder 104 at the outer ends of the extensions 120. The first edge 122 transforms into a second edge 124 having an inclination in the rearward proximal direction as seen in FIG. 13. The second edge 124 then transforms into a third edge 126 again being generally parallel with the extension of the medicament container holder 104. The extensions 120 are further arranged with tongues 128 that extend in the rear direction of the medicament container holder 104. The tongues 128 have a somewhat outwardly inclination of their free ends and have resilient properties.

The proximal housing part 10 is further arranged with two guide walls 130, FIG. 8, between which the medicament container holder 104 is placed. One of the guide walls 130 closest to the activating element 48 is arranged with a spring element 144 that in the embodiment shown is a resilient tongue, the function of which will be described below. At an end of the guide walls 130 vertical grooves 132 are arranged, positioned opposite each other. Between the grooves 132 a generally circular passage 134 is arranged in the proximal housing part 10. A needle assembly 136, FIGS. 12 and 13, is arranged to be positioned between the guide walls 130. The needle assembly 136 is generally tubular and is arranged with two oppositely positioned, generally rectangular, guide elements 138, FIG. 13, which guide elements 138 are designed to fit into the grooves 132 of the guide walls 130, enabling movement but preventing rotation of the needle assembly 136. The needle assembly 136 is arranged with a downwardly directed injection needle part 140, FIG. 13. Further on a side surface of the needle assembly 136 a piercing needle part 142 is arranged and directed towards the medicament container holder 136.

A passage 146 is arranged inside the needle assembly 136 between the injection needle part 140 and the piercing needle part 142, creating a communication between them. In this regard, it is to be understood that the injection needle part 140 and the piercing needle part 142 could be formed by a single tubular element sharpened in both ends and arranged in the needle assembly 136. Resilient bellows 148A, 148B, FIG. 12, are arranged surrounding each of the needle ends that are outside the needle assembly 136, in the initial position of the needle assembly 136, keeping them sterile. Coaxial with and arranged surrounding the needle assembly 136 is a generally tubular needle guard 150, FIG. 14. Longitudinal cut-outs 152 are arranged in the tubular needle guard 150, in which the guide elements 138 of the medicament member holder 136 fit. The needle guard 150 extends through the passage 134 in the proximal housing part 10. In the initial position of the medicament delivery needle guard 150, it is prevented from any movement due to inwardly directed ledges 156 of the extensions 120 of the medicament container holder 104 fitting into slits 158 on the distal part of the needle guard 150.

A bottom part of the needle guard 150 is arranged with a generally circular support plate 160, which support plate 160 is arranged with a central hole 162 somewhat larger than the diameter of the injection needle part 140. The support plate 160 is in its initial position placed in a recess 164 on the outer surface of the first housing part 10, surrounding the passage 134, so that the outer surface of the support plate 160 is generally in the same plane as the outer surface of the proximal housing part 10. A needle guard spring 166 is arranged between an inner surface of the support plate 160 and the guide elements 138 of the needle assembly 136. The needle guard 150 is further arranged with wedge-shaped stop ledges 168 on its outer surface that have end surfaces 170 directed downwards. The needle guard 150 is further arranged with upwardly directed tongues 172 that are flexible in the generally radial direction. The tongues 172 are arranged with outwardly directed wedge-shaped protrusions 174.

In general, it can be noted that the rotator 62, the drive spring 76, the gear teeth 100, the gear rack 102 and the medicament container holder 104 form both a penetration mechanism as well as a medicament container connection mechanism. Further, it may be noted that the teeth 100, the gear rack 102, the medicament container holder 104 and the extension can be regarded as drive elements for causing a penetration movement of the needle assembly 136.

Figure 15:
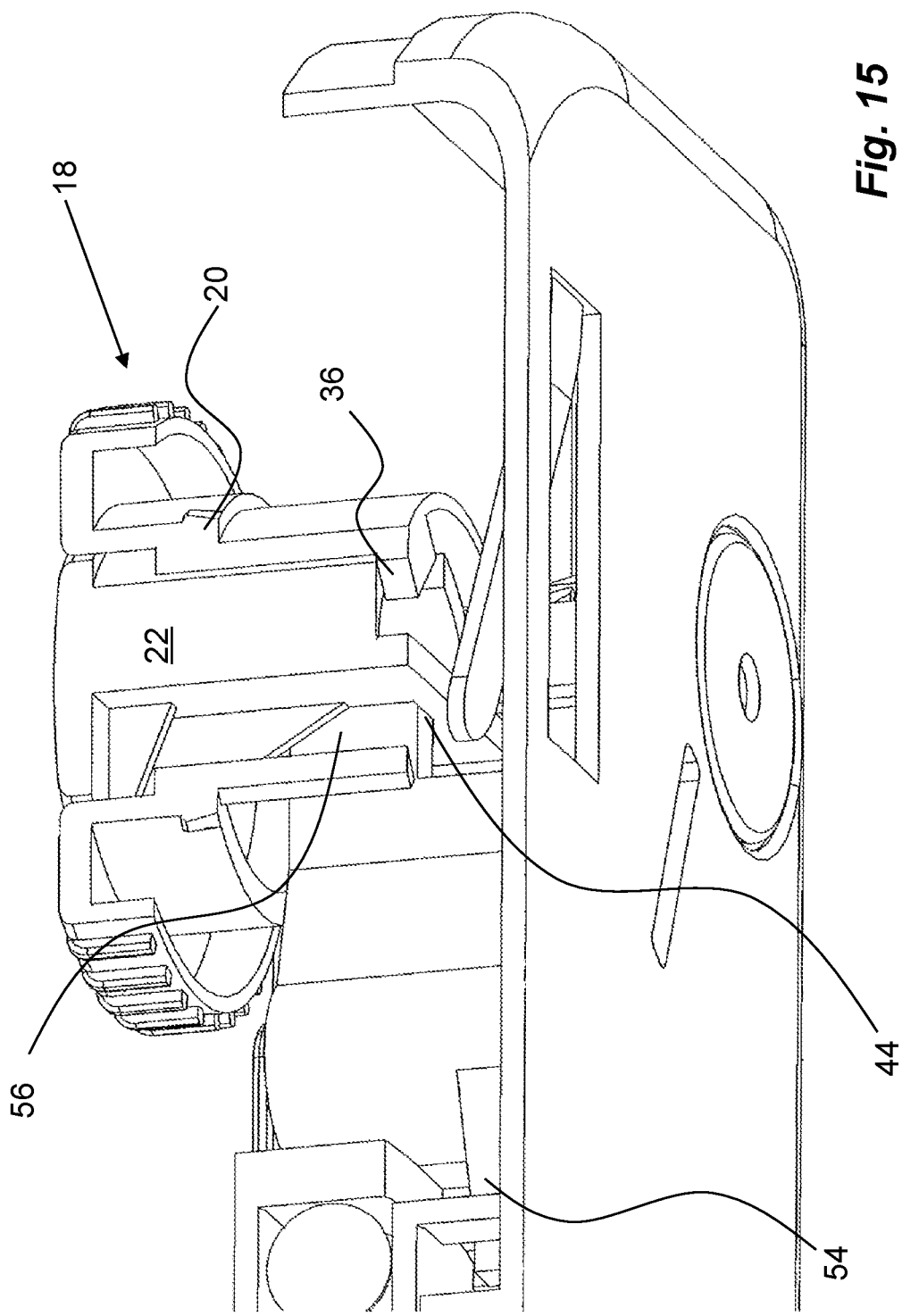
FIG. 15 is a detailed cross-sectional view of an activation unit comprised in the medicament delivery device of FIG. 1.

The device is intended to function as follows. When the device is delivered to a user, the clock spring 76 is in a tensioned state. It is held in this tensioned state by the first arm 54 of the activating element 48 engaging with the cut-out 68 of the rotator 62 of the drive unit 60, FIG. 2. The first arm 54 is in turn held stationary in that the second arm 56 is in engagement with the second cut-out 44 of the activator 22, FIG. 15. The activator 22 is however prevented from being depressed due to that the lock element 20 is positioned with an arrow on the activator ring pointing at the "0" indicia, in which position the inwardly directed protrusion 36 of the lock element 20 is in contact with a proximally directed end surface of the activator 22, FIG. 15.

Figure 16:
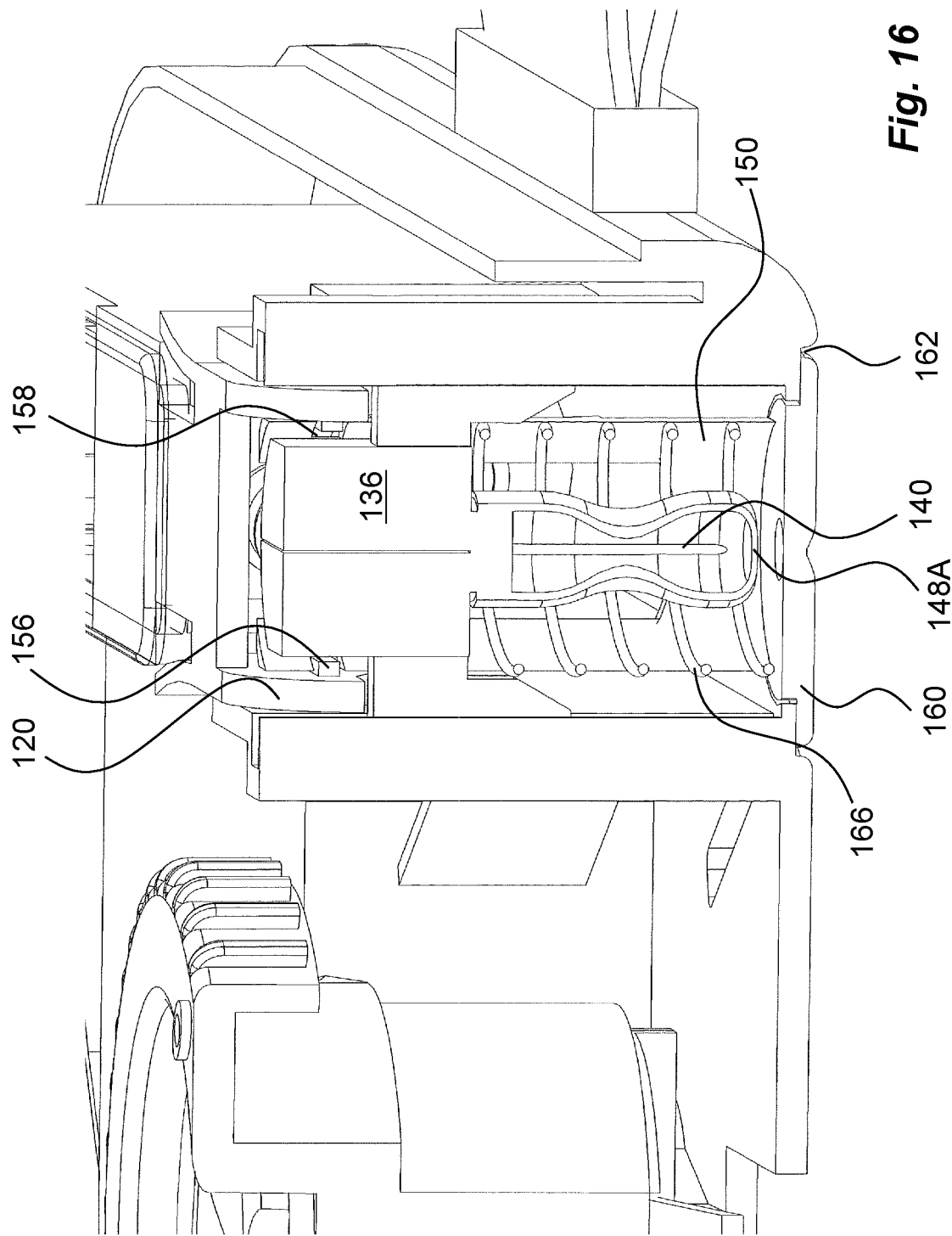
FIG. 16 is a detailed cross-sectional view of a needle assembly comprised in the medicament delivery device of FIG. 1, and FIGS. 17, 18, 19, 20, 21, 22, 23, 24, 25 and 26 are different views of functional stages of the medicament delivery device of FIG. 1.

The needle guard 150 is locked in the retracted position, FIG. 16, by the ledges 156 of the extensions 120 fitting into the slits 158 of the distal end of the needle guard, with the support plate 160 placed in the recess 164. Further, the needle assembly 136 with the injection needle part 140 is held in the retracted position inside the housing by the needle guard spring 166, FIG. 16. As seen in FIG. 16, the injection needle is protected by the bellows 148A.

The user opens the lid 114 and places a medicament container 106 in the medicament container holder 104 and replaces the lid 114. The user then attaches the housing with the proximal housing part 10 against a body part. The device may be attached in different ways, such as with a strap, band 16 or the like as shown. It is however to be understood that other types of attachments may be feasible, such as an adhesive layer on the surface of the proximal housing part 10, providing releasable attachment to a body part of a user.

Figure 17:
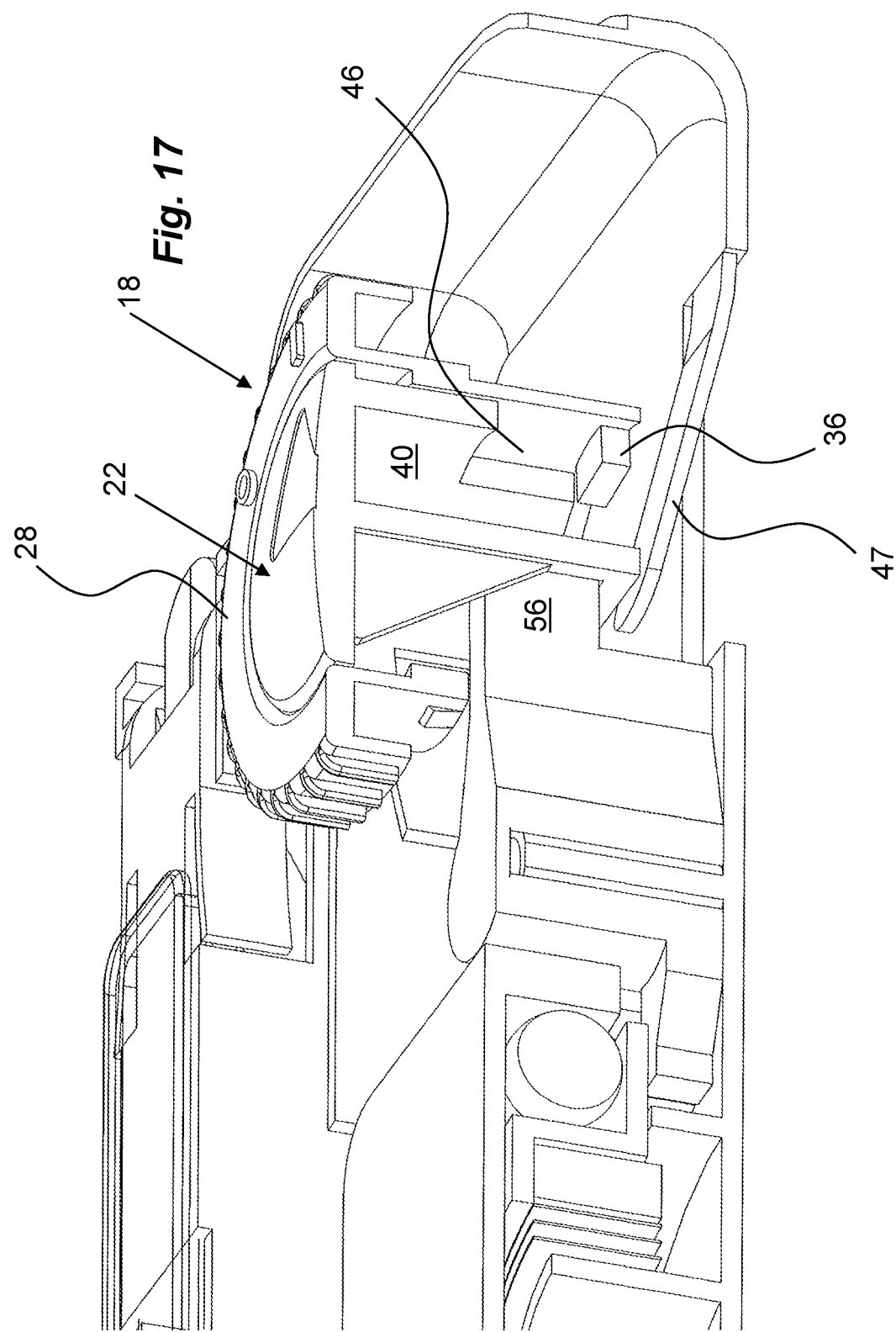
Figure 18:
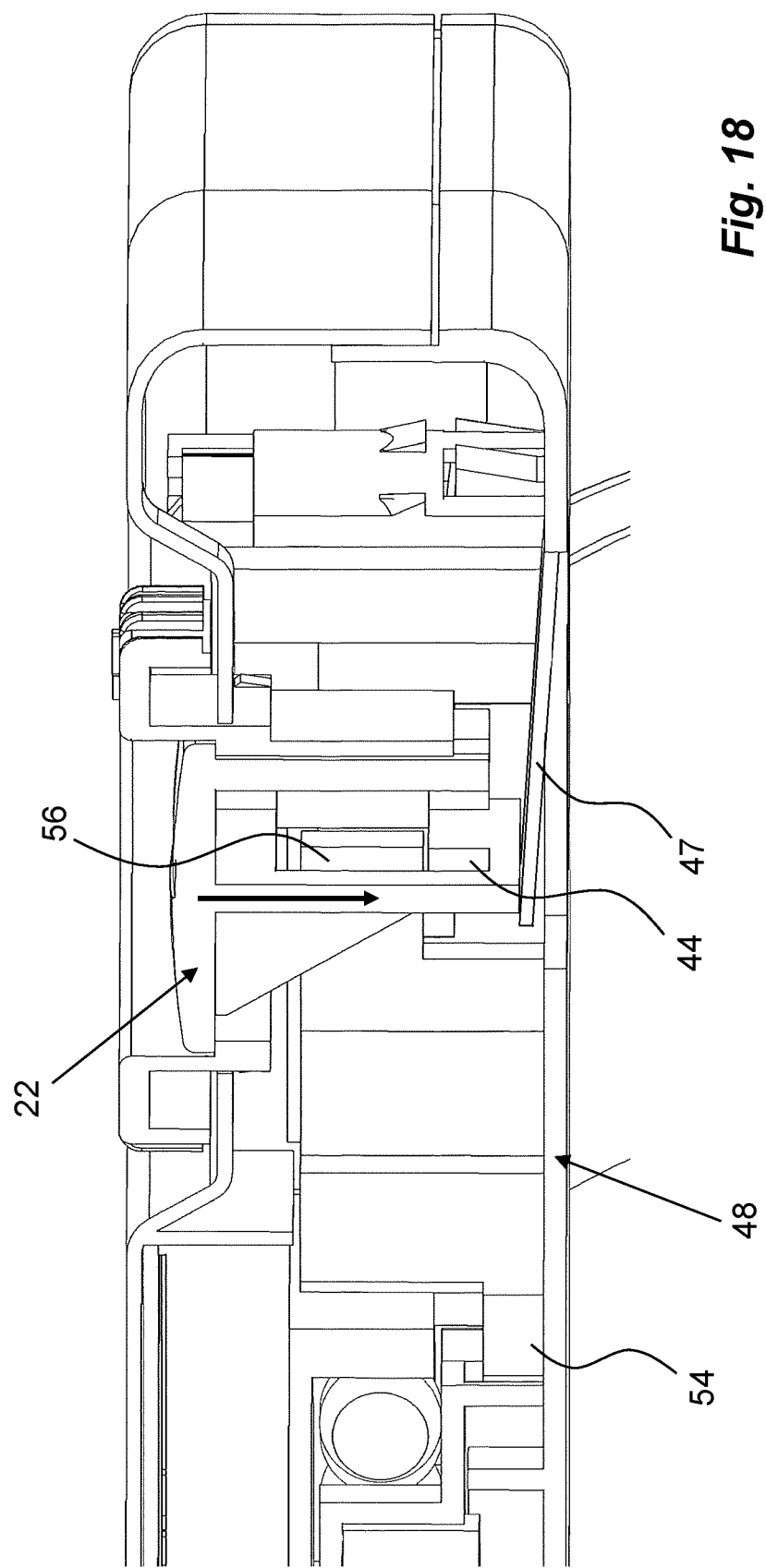

When the device is to be used, the user turns the grip ring 28 of the lock element 20 from the "0" position to the "1", FIG. 17, in which the device can be activated. The rotation of the lock element 20 will move the inwardly directed protrusion 36 of the lock element 20 to be in line with the third cut-out 46 of the body 40 of the activator 22, i.e. the activator 22 may be depressed. When it is time to start an injection the user depresses the activator 22 into the housing against the spring force of the resilient member 47. This movement of the activator 22 will cause the second arm 56 to move out of engagement with the second cut-out 44 of the activator 22, FIG. 18, whereby the activating element 48 is free to rotate around the post 52 due to the force from the rotator 62 acting on the first arm 54 by the clock spring 76. This will then cause the first arm 54 to move out of contact with the rotator 62.

Figure 19:
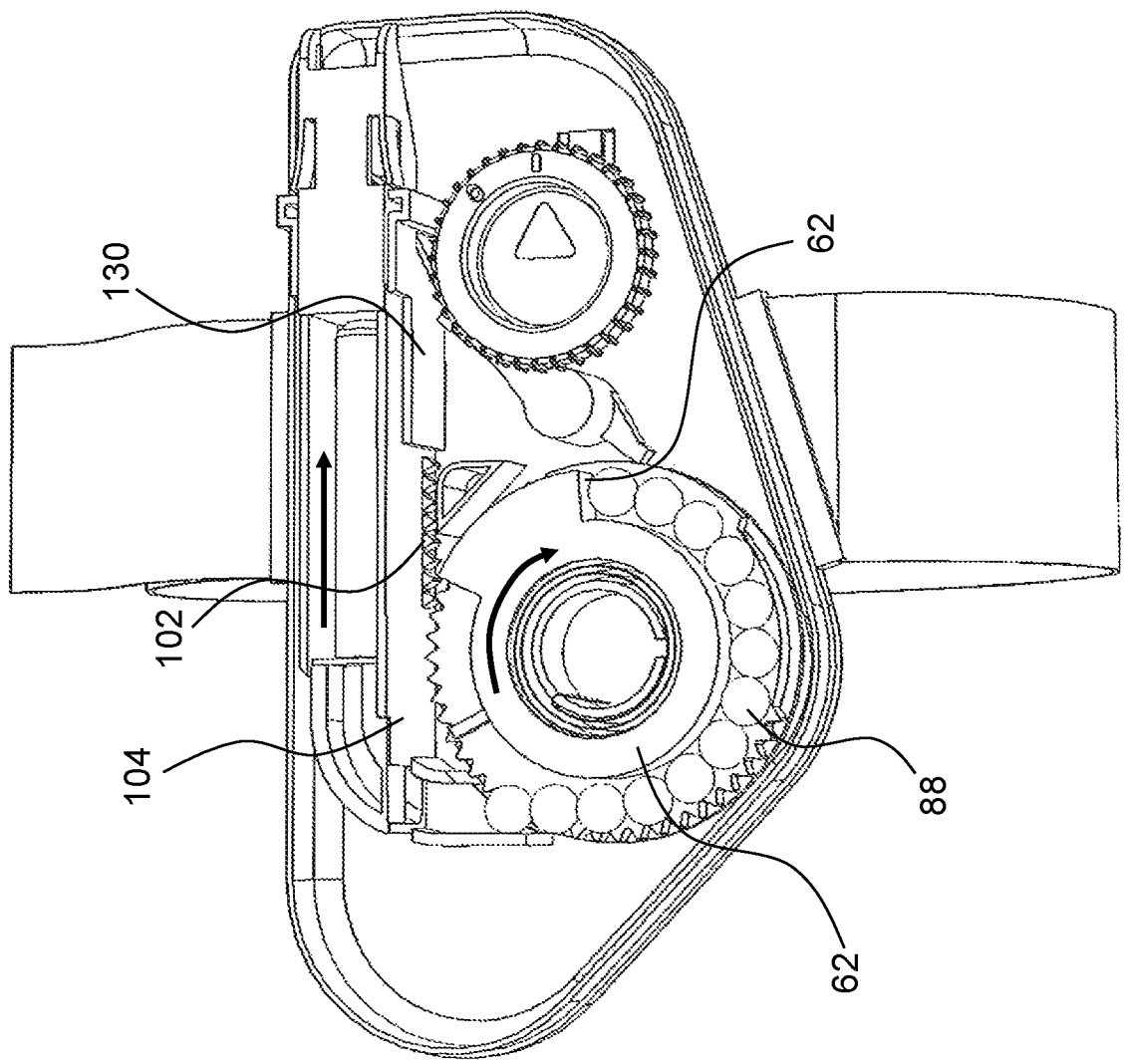
Figure 20:
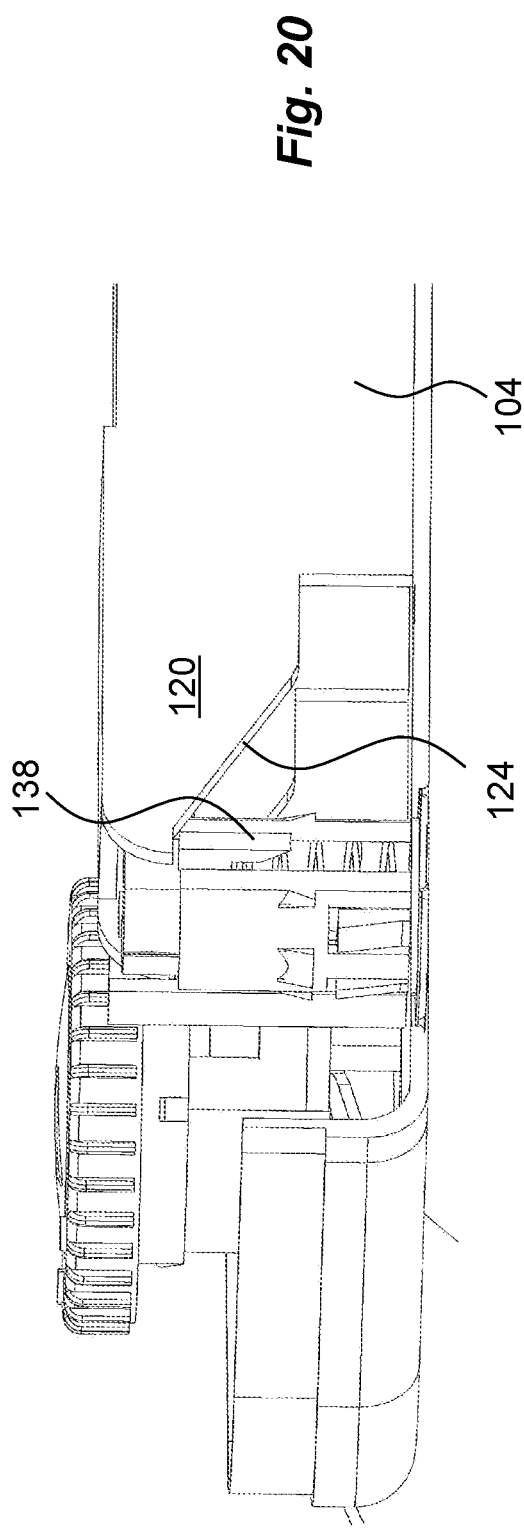

The rotation of the rotator 62 will cause its gear teeth 100 on the outer surface to interact with the gear rack 102 on the side of the medicament container holder 104 as seen in FIG. 9. This in turn will cause the medicament container holder 104 to move forward guided by the guide walls 130 of the proximal housing part 10, FIG. 19. The inclined second edges 124 of forwardly directed extensions 120 will act on the guide elements 138 of the needle assembly 136 as transfer elements, FIG. 20, and since the guide elements 138 are placed in the grooves 132 of the guide walls 130, the needle assembly 136 will be moved in the proximal direction, whereby the bellows 148A surrounding the injection needle part 140 will be depressed and penetrated by the injection needle part 140, FIG. 21. Further movement of the needle assembly 136 will cause a penetration of the patient by the injection needle part 140. The penetration movement is stopped when the guide elements 138 reach the third edges 126 of the extensions 120 of the medicament container holder 104, FIG. 22.

Figure 23:
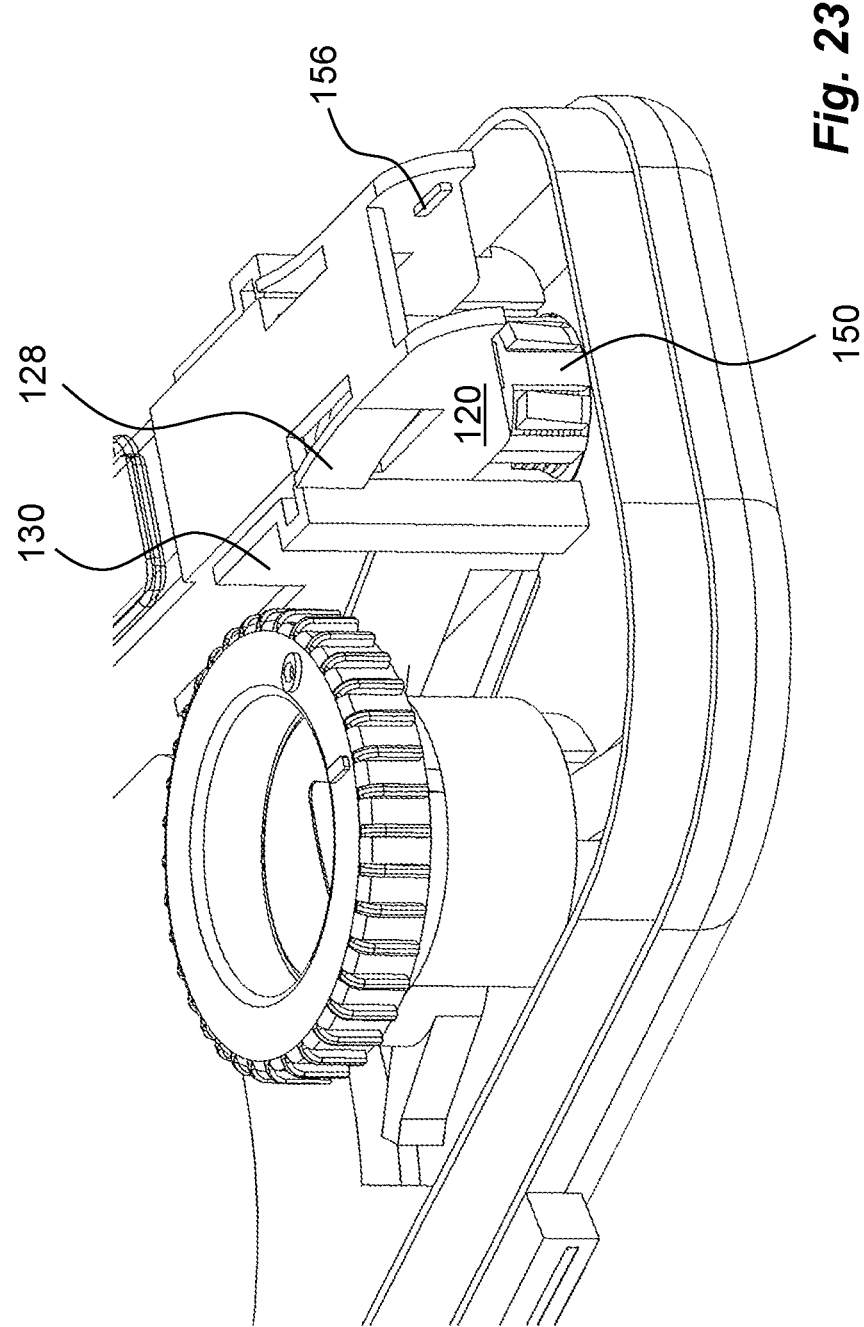

At this position of the medicament container holder 104, the tongues 128 on the extensions 120 have past the guide walls 130 and due to the slight inclination and the resilient properties of the tongues 128 they have flexed outwardly, preventing any movement towards the initial position of the medicament container holder 104, FIG. 23. During the penetration movement of the needle assembly 136 the needle guard spring 166 will be depressed by the guide elements 138 of the needle assembly 136, FIG. 21. The needle guard 150 has been released in that the ledges 156 of the extensions 120 of the medicament container holder 104 have been moved out of the slits 158 of the needle guard 150 as seen in FIG. 23. However, the needle guard 150 is prevented from moving in that the support plate 160 of the needle guard 150 is in contact with the body of the user.

Figure 21:
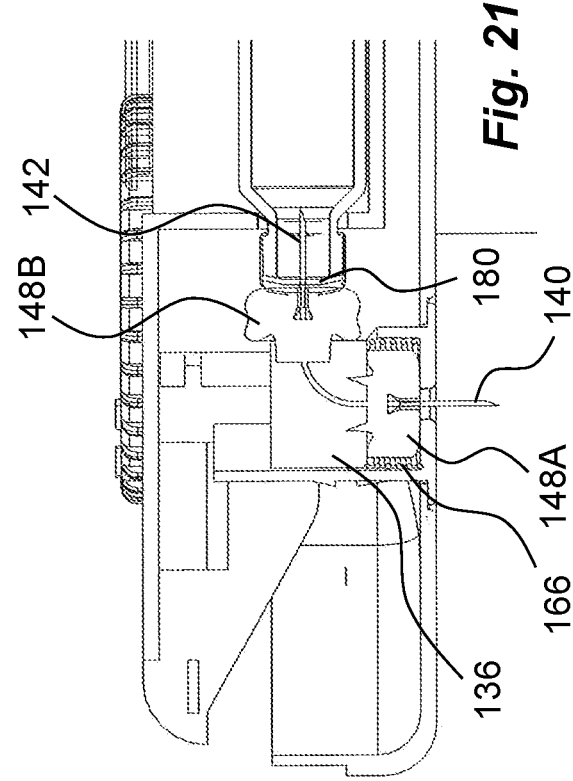
Figure 22:
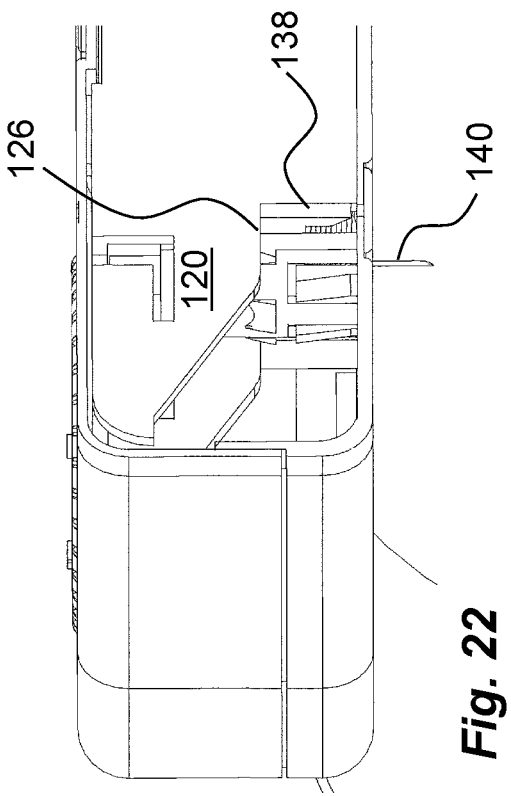

In addition, the movement of the medicament container holder 104 will cause the front end of the medicament container 106 to move towards and come in contact with the bellows 148B of the piercing needle part 142 wherein the bellows 148B will be depressed and pierced by the piercing needle part 142 and further movement will cause the piercing needle part 142 to penetrate a septum 180 of the medicament container, creating a passage between the interior of the medicament container 106 and the injection needle part 140, FIG. 21.

Figure 24:
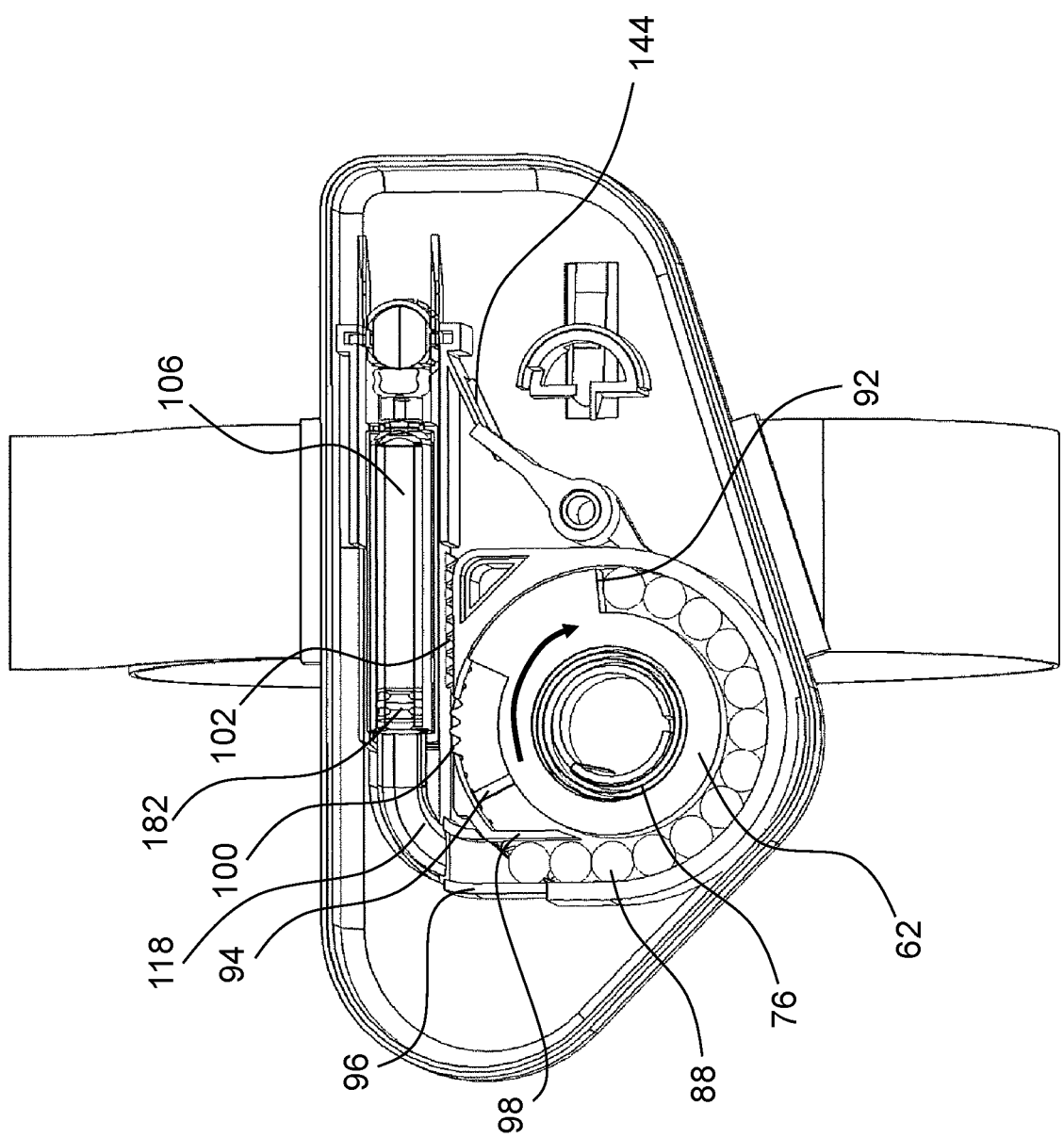

The rotator 62 will continue to rotate, but now the gear rack 102 has been moved out of contact with the gear teeth 100 of the rotator 62, as seen in FIG. 24. Due to the side wall 92 of the rotator 62, when the rotator 62 is rotating, driven by the drive spring 76, the rotator 62 will push the row of balls 88 in the channel 91 formed by the hub 82 of the rotator and the lid 90. When the rotator 62 rotates, the stop ledge 94 will move out of blocking engagement with the foremost ball 88, FIG. 24. The balls 88 will now be pushed along the guide walls 96, 98 and into the curved channel 118 until the foremost ball 88 comes in contact with a stopper 182 of the medicament container 106.

Figure 25:
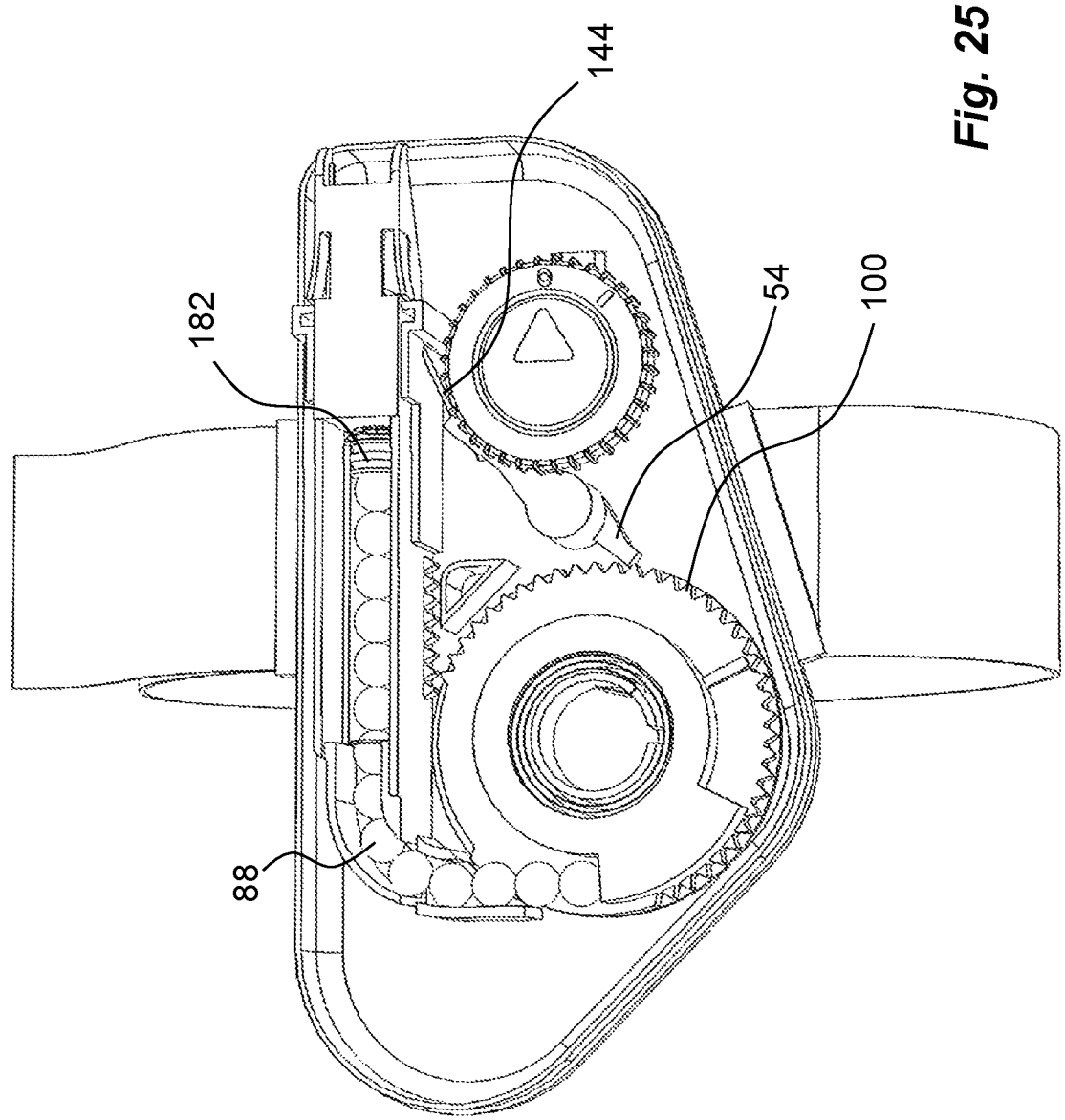

Continuing movement of the row of balls 88 will move the stopper 182 in the forward direction inside the medicament container 106 thereby causing an injection of medicament through the injection needle part 140 into the injection site, FIG. 25. During the rotation of the rotator 62 for performing the injection, the first arm 54 of the activating element 48 will be in contact with the gear teeth 100 of the rotator 62 and be pressed in contact by the spring element 144 acting on the second arm 56. The contact of the first arm 54 will cause a clicking sound and maybe also a tactile feeling when the rotator 62 is rotating, which will indicate to a user that the injection is in progress.

When the injection sequence has come to an end due to that the stopper 182 is in the most forward position inside the medicament container 106, the rotator 62 will stop rotating, whereby the indication will stop. The user can then remove the device from the injection site. This will now cause the needle guard 150 to extend from the proximal housing part 10 due to the force from the needle guard spring 166, FIG. 26. The extending movement will cause the wedge-shaped protrusions 174 of the flexible tongues 172 to pass the edge of the passage 134 of the proximal housing part 10 and flex out afterwards. The extending movement stops when the stop ledges 168 hit the inner surface of the proximal housing part 10. The needle guard 150 is thus locked from movement dues to the stop ledges 168 and the protrusions 174 of the tongues 172. The device may now be discarded in a safe way.

It is to be understood that the embodiment described above and shown in the drawings is to be regarded only as a non-limiting example of the disclosure and that it may be modified in many ways within the scope of the patent claims.

The invention claimed is:

1. A medicament delivery device comprising
    a housing;
    a medicament container holder arranged to accommodate a medicament container;
    a needle assembly comprising an injection needle part and a penetration needle part, wherein the extension of the injection needle part and the extension of the penetration needle part are angled generally 90 degrees;
    a first resilient bellows around the injection needle part of the needle assembly and a second resilient bellows around the penetration needle part of the needle assembly;
    a penetration mechanism arranged to move the needle assembly in a direction generally coinciding with the extension of the injection needle part between an initial position of the injection needle part inside said housing to a penetration position with the injection needle part extending outside said housing, wherein movement via the penetration mechanism causes the injection needle part to puncture the first resilient bellows; and
    a medicament container connection mechanism arranged to move the medicament container holder and the medicament container in a direction generally coinciding with the penetration needle part for creating a flow passage from the interior of the medicament container to an outlet of the injection needle part, wherein movement via the medicament container connection mechanism causes the penetration needle part to puncture the second resilient bellows and a septum of the medicament container, and wherein puncturing the second resilient bellows and the septum of the medicament container creates the flow passage from the interior of the medicament container to an outlet of the injection needle part.

2. The medicament delivery device according to claim 1, comprising a drive mechanism comprising a rotator, arranged to be rotated by a tensioned drive spring, and drive elements arranged between said rotator and said needle assembly for causing a penetration by said injection needle part.

3. The medicament delivery device according to claim 2, wherein said drive elements comprise said medicament container holder operatively connected between said rotator and said needle assembly.

4. The medicament delivery device according to claim 3, wherein said medicament container holder comprises a transfer element acting on said needle assembly such that movement of the medicament container holder by said rotator causes a penetrating movement of said needle assembly.

5. The medicament delivery device according to claim 4, wherein said transfer element comprises surfaces that are inclined in relation to the movement direction of said medicament container holder and the movement direction of said needle assembly, which inclined surfaces are acting on guide elements of said needle assembly.

6. The medicament delivery device according to claim 2, wherein said drive mechanism comprises teeth on said rotator acting on a toothed rack on said medicament container holder.

7. The medicament delivery device according to claim 2, wherein said drive mechanism further comprises a number of discrete elements placed around the circumference of the rotator and operatively connected to said rotator, wherein rotation of said rotator causes said discrete elements to move and to act on a stopper of said medicament container for expelling a dose of medicament.

8. The medicament delivery device according to claim 7, wherein said drive mechanism further comprises guide elements for guiding said discrete elements between said rotator and said medicament container holder for acting on said stopper.

9. The medicament delivery device according to claim 2, wherein the rotator is designed such that that interaction with said medicament container holder for performing a penetration is completed when said discrete elements begin acting on said stopper.

10. The medicament delivery device according to claim 7, wherein said discrete elements comprise spherical bodies.

11. The medicament delivery device according to claim 2, further comprising an activation unit operatively connected to said rotator for releasably holding said drive spring in a tensioned state.

12. The medicament delivery device according to claim 11, wherein said activation unit comprises a manually operable activator, which upon manual activation, releases said rotator.

13. The medicament delivery device according to claim 12, wherein said activation unit further comprises a lock element for releasably locking said activator.

14. The medicament delivery device according to claim 11, wherein said activation unit further comprises an activating element in the form of a pivoting arm, wherein one end of the arm is releasably engaging said rotator and the other end of the arm is releasably engaging said activator.

15. The medicament delivery device according to claim 14, wherein said pivoting arm, after release of said rotator, is in contact with a profiled surface of said rotator for creating an indication of the operation of the medicament delivery device.

16. A medicament delivery device comprising:
a housing;
a medicament container holder arranged to accommodate a medicament container;
a needle assembly comprising an injection needle part and a penetration needle part, where an extension of the injection needle part an extension of the penetration needle part forms an angle of generally 90 degrees;
a first resilient bellows around the injection needle part of the needle assembly and a second resilient bellows around the penetration needle part of the needle assembly;
a rotator operatively engaged with the medicament container and a tensioned drive spring that rotates the rotator to cause the injection needle to move relative to the housing from an initial position of the injection needle part inside the housing to a penetration position with the injection needle part extending outside the housing, wherein movement via the rotator causes the injection needle part to puncture the first resilient bellows; and
a medicament container connection mechanism arranged to move the medicament container holder and the medicament container in a direction generally coinciding with the penetration needle part for creating a flow passage from the interior of the medicament container to an outlet of the injection needle part, wherein movement via the medicament container connection mechanism causes the penetration needle part to puncture the second resilient bellows and a septum of the medicament container, and wherein puncturing the second resilient bellows and the septum of the medicament container creates the flow passage from the interior of the medicament container to an outlet of the injection needle part.

17. The medicament delivery device of claim 16, further comprising a transfer element having an inclined surfaces that engages a guide element of said needle assembly to cause the injection needle assembly to move to the penetration position.

18. The medicament delivery device according to claim 16, further comprising a drive mechanism having a plurality of discrete elements located around the circumference of and operatively connected to a rotator, where when the rotator is rotated the discrete elements move and act on a stopper located inside of the medicament container to expel medicament.

19. The medicament delivery device according to claim 18, wherein the drive mechanism further comprises guide elements for guiding the discrete elements between the rotator and the medicament container holder to act on the stopper.

20. The medicament delivery device according to claim 19, further comprising an activation unit operatively connected to the rotator for releasably holding a drive spring in a tensioned state.

* * * * *